(12) United States Patent
Hart et al.

(10) Patent No.: US 9,995,667 B2
(45) Date of Patent: *Jun. 12, 2018

(54) PORTABLE DEVICE FOR DETECTING AND MEASURING PARTICLES ENTRAINED IN THE AIR

(71) Applicant: TZOA/Clad Innovations Ltd., San Francisco, CA (US)

(72) Inventors: Kevin R. Hart, Port Coquitlam (CA); Taylor Cooper, Coquitlam (CA); Vlad Lavrovsky, Vancouver (CA); Div Gill, Vancouver (CA); Justin Lam, Vancouver (CA)

(*) Notice: Subject to any disclaimer, the term of this patent is extended or adjusted under 35 U.S.C. 154(b) by 50 days.

This patent is subject to a terminal disclaimer.

(21) Appl. No.: 15/135,152

(22) Filed: Apr. 21, 2016

(65) Prior Publication Data

US 2017/0023457 A1 Jan. 26, 2017

Related U.S. Application Data

(60) Provisional application No. 62/151,335, filed on Apr. 22, 2015.

(51) Int. Cl.
*G01N 15/06* (2006.01)
*G01N 15/02* (2006.01)
(Continued)

(52) U.S. Cl.
CPC ......... *G01N 15/06* (2013.01); *G01N 15/0205* (2013.01); *G01N 15/1459* (2013.01);
(Continued)

(58) Field of Classification Search
CPC ............... G01N 21/53; G01N 15/0211; G01N 2015/0693; G01N 2001/2276; G01N 2201/0221; G01N 2201/0612
See application file for complete search history.

(56) References Cited

U.S. PATENT DOCUMENTS 3,535,531 A * 10/1970 Neitzel .................. G01N 21/53
250/574
3,819,269 A 6/1974 Duvall et al.
(Continued)

FOREIGN PATENT DOCUMENTS

CN 203310444 U 11/2013
WO 2009144508 12/2009

OTHER PUBLICATIONS

Srinivas Devarakonda, Parveen Sevusu, Hongzhang Liu, Ruilin Liu, Livid Iftode, Badri Nath, Real-time Air Quality Monitoring Through Mobile Sensing in Metropolitan Areas (research paper), Department of Computer Science, Rutgers University, Piscataway, NJ USA. 2013.

(Continued)

*Primary Examiner* — Dominic J Bologna
(74) *Attorney, Agent, or Firm* — Gina M. Lupino

(57) ABSTRACT

A portable ambient air quality monitor having an enclosure to enclose and protect the monitor from an ambient environment and an airflow intake for controllably allowing ambient air to enter the monitor. A photodiode is disposed at a location downstream from a fan. The airflow from the fan is laminarized by a mesh or baffle to allow a thin stream of air to flow over the photodiode. A sensing region is defined by an intersection of an airflow sampling path and an optical path. The sensing region is also disposed above the photodiode. The airflow sampling path is configured to receive laminar airflow from the airflow intake and for directing the laminar airflow into the sensing region. A light beam is generated from a laser to reflect the light beam for reducing the required area of the sensing region to detect and measure the particles floating in the ambient air.

14 Claims, 8 Drawing Sheets

(51) Int. Cl.
*G01N 21/53* (2006.01)
*G01N 21/47* (2006.01)
*G01N 15/14* (2006.01)

(52) U.S. Cl.
CPC ........ *G01N 21/53* (2013.01); *G01N 21/4785* (2013.01); *G01N 2015/0693* (2013.01); *G01N 2015/1486* (2013.01); *G01N 2015/1493* (2013.01); *G01N 2201/0221* (2013.01); *G01N 2201/0612* (2013.01); *G01N 2201/0642* (2013.01)

(56) References Cited

U.S. PATENT DOCUMENTS

| | | | |
|---|---|---|---|
| 3,833,305 A * | 9/1974 | Porter | G01N 21/15 250/573 |
| 4,783,599 A | 11/1988 | Borden | |
| 5,085,500 A | 2/1992 | Blesener | |
| 5,132,548 A | 7/1992 | Borden et al. | |
| 5,262,741 A | 11/1993 | Kitakubo | |
| 5,534,999 A | 7/1996 | Koshizuka | |
| 5,684,585 A | 11/1997 | Girvin et al. | |
| 5,870,190 A | 2/1999 | Unger | |
| 6,404,494 B1 * | 6/2002 | Masonis | G01N 21/53 250/574 |
| 7,088,447 B1 | 8/2006 | Bates et al. | |
| 8,009,290 B2 | 8/2011 | Unger | |
| 8,494,773 B2 | 7/2013 | Jensen et al. | |
| 8,603,772 B2 | 12/2013 | Debreczeny et al. | |
| 2004/0083064 A1 * | 4/2004 | Wyatt | G01N 1/2202 702/28 |
| 2007/0103696 A1 * | 5/2007 | Pohlmann | G03F 7/70775 356/498 |
| 2008/0106736 A1 | 5/2008 | Graves et al. | |
| 2012/0122084 A1 * | 5/2012 | Wagner | C12N 5/0612 435/6.1 |
| 2013/0317379 A1 * | 11/2013 | Brimer | A61B 5/087 600/538 |
| 2014/0152986 A1 * | 6/2014 | Trainer | G01N 15/0205 356/336 |
| 2014/0163927 A1 | 6/2014 | Molettiere et al. | |
| 2014/0243617 A1 | 8/2014 | LeBoeuf et al. | |
| 2015/0153275 A1 * | 6/2015 | Park | G01N 33/0036 356/336 |
| 2016/0025628 A1 * | 1/2016 | Kim | G01K 13/02 356/72 |

OTHER PUBLICATIONS

Matthias Budde, Rayan El Masri, Till Riedel, Michael Beigl; Enabling Low-Cost Particulate Matter Measurement for Participatory Sensing Scenarios; Teco, Karlsruhe Institute of Technology (KIT), Karlsruhe, Germany; 2013.

Anna Morpurgo, Federico Pedersini, and Alessandro Reina; A low-cost instrument for environmental particulate analysis based on optical scattering; Department of Information Science, Universita degli studi di Milano Via Comelico 39141, I-20135 Milano, Italy; 2012.

\* cited by examiner

Section A-A

Section B-B

PORTABLE DEVICE FOR DETECTING AND MEASURING PARTICLES ENTRAINED IN THE AIR

PRIORITY CLAIM

This non-provisional application claims priority to Provisional Patent Application Ser. No. 62/151,335, entitled "Measurement of Particulate Matter through Optical Techniques", filed on Apr. 22, 2015.

TECHNICAL FIELD

The present invention relates generally to a device for detecting and measuring particles entrained in a fluid by measuring light scattering from the particulate matter using optical techniques. In particular, the present invention may be used to measure particulate matter floating in ambient air.

BACKGROUND OF THE INVENTION

There is a growing market demand for inexpensive air quality monitors for both research and personal health. Airborne particulate matter is among the deadliest forms of air pollution. The risk of lung cancer is greatly increased by the concentration of particulate matter below PM10. Asthma, cardiovascular disease, respiratory diseases and birth defects have also been associated with increases in airborne particulate matter concentration. In addition, these conditions are a detriment to the economy, resulting in thousands of workers on sick leave per day and billions of dollars straining health care systems around the world. Environmental researchers often do not have the budget to purchase multiple devices to develop data maps in order to monitor these adverse environmental conditions.

Airborne particulate matter can be measured gravimetrically to determine the mass concentration of matter in aerosol. However, this method is time consuming and often requires manual procedures. More recently, particulate matter has been measured with a Light Scattering Aerosol Spectrometer, or LSAS. These sensors count and size particles individually, respond quickly to changing environmental conditions, and can continuously monitor conditions for months without user intervention.

Typically, a LSAS works by drawing a sample of air through a beam of light. The beam of light is scattered due to the particles entrained in the sample of air. Optical collection systems direct the scattered light to a photodiode, which in turn converts the collected light into current that is then amplified into an analog voltage signal. The voltage signal is typically a pulse, where the pulse width and amplitude are proportional to the light intensity and particle diameter. The particle size, incident light, and other physical characteristics may be determined from this pulse. The concentration of particles entrained in the sample of air may also be determined by analyzing the pulses over time.

An inlet is typically used to draw a sample of air through the sensor. It may take the form of a nozzle or jet with either a round or rectangular profile. The round inlet provides a larger cross-section and requires a lower vacuum than the rectangular profile, resulting in lower power consumption. Although the round inlet is simpler to implement, the circular airflow has reduced uniformity and higher variations in light intensity across the intersection of the airflow and light beam. The rectangular profile provides better particle resolution because the flattened and wide airflow moves at a fairly uniform velocity across its area and intersects the light beam at the most intense and uniform region. However, the rectangular profile is more complex and expensive to manufacture.

As a particle passes through the laser, light is reflected and focused by the collection optics onto a photodiode. One difficulty in collection optics is the dependency of scattered light direction on particle size. Ideally, the sensor assembly captures all light and focuses it on to the photodiode while removing any unwanted light. Smaller particles typically scatter in the forward direction, whereas larger particles scatter at backward and right angles. If particles are significantly smaller than the cross-section of the light beam, they may not generate a high enough pulse to be distinguishable from signal noise. Border zone error occurs when particles straddle the optical border of the sensing zone, resulting in only a fraction of the light to be scattered. Coincidence error can occur with high particle number concentrations, where two or more particles are simultaneously present in the sensing zone.

Another difficulty lies in transport losses in the sampling tubing. The sampling system is part of a measurement chain and follows aerosol extraction, transport, and processing; the quality of the overall measurement is determined by the weakest element of this chain. The aerosol particles in the transport tubing can be affected by diffusion, sedimentation, inertia, condensation effects, and aggregation or coagulation. Aggregation or coagulation is a function of the collision and adhesion of particles. This results in a larger particle diameter and a smaller particle number concentration with constant mass concentration.

Current LSAS sensors are often complex and difficult to manufacture, and airborne particulate monitoring using them can be expensive, laborious, or inconvenient. In addition, airborne particulate matter has a strong link to lung cancer and cardiovascular disease. Accordingly, this results in a need for a low cost, effective method of monitoring and tracking environmental conditions.

SUMMARY OF THE INVENTION

The present invention provides an improved method for detecting and measuring particles entrained in a fluid. This embodiment of the invention contains the following components, known to those skilled in the art of laser scattering aerosol spectrometry: an enclosure, a fan, a laser and a printed circuit board (PCB). The enclosure consists of components for: containing the sensor, baffling for stray light, baffling for air flow control and user interaction. The PCB has the following components: photodiode, an amplifier circuit, an ADC, an MCU or DSP and control electronics. Other embodiments of the device may contain a plurality of any of these components.

In one embodiment of the invention, the light scattering device draws a continuous sample of fluid through a light beam by means of a vacuum created with an axial or centrifugal fan. The light beam geometry is reflected such that the beam length and geometry is maintained while reducing the required area. The photodiode has a large sensing area, thus reducing the need for optical collection systems to collect the light scattered by entrained particles within the sensing volume. In other embodiments of the invention, an optical collection system is included to focus the scattered light on to the photodiode. Due to the large sensing area of the photodiode, it is essential that the capacitance of the photodiode be controlled; otherwise the device response time is reduced to the point that small particles, with short transit times, cannot be detected. Thus there are two methods of reducing photodiode capacitance, the use of photodiodes with intrinsically low capacitance due to their internal structure and chemistry, and the use of electrical biasing that reduces their effective capacitance. Careful management of the bias voltage can result in very low activation thresholds.

A further embodiment of the invention provides a method for detecting and measuring particles in an ambient environment (See FIG. 9). This method includes the steps of enclosing a portable air quality monitor from the ambient environment 905; receiving ambient air in the monitor, the monitor has a controlled airflow intake for receiving the ambient air 910; forming an airflow sampling path and laminarizing the airflow in the sampling path using a mesh or a baffle to reduce airflow turbulence and to allow a thin stream of the laminarized air to flow into a sensing region 915; directing the laminar airflow into the sensing region 920; sensing the flow of the ambient air in the sensing region, the sensing region including a photodiode illuminated by the laser beam defining an optical path, the sensing region being defined by the intersection of the airflow sampling path and the optical path 925; and reducing the light beam to reduce the area of the sensing region to detect and measure particles entrained in the ambient air 930.

The detailed description of the present invention covers many improvements to the traditional LSAS, including an approach for miniaturizing a standard LSAS geometry and its limitations; methods for implementation of a self-cleaning device; techniques for increasing the sensitivity of the LSAS and reducing background noise; methods for reducing power consumption of the device; methods for improved signal smooth, baseline subtraction, peak detection, particle sizing and counting.

Consequently, for a better understanding of the present invention, its functional advantages and the specific objects attained by its uses, reference should be made to the accompanying drawings, claims and descriptive matter in which there are illustrated preferred embodiments of the invention.

DETAILED DESCRIPTION

The following detailed description is of the best currently contemplated modes of carrying out various embodiments of the invention. The description is not to be taken in a limiting sense, but is made for at least the purpose of illustrating the general principles of the invention, since the scope of the invention is best defined by the appended claims.

Enclosure

Figures 1, 2:
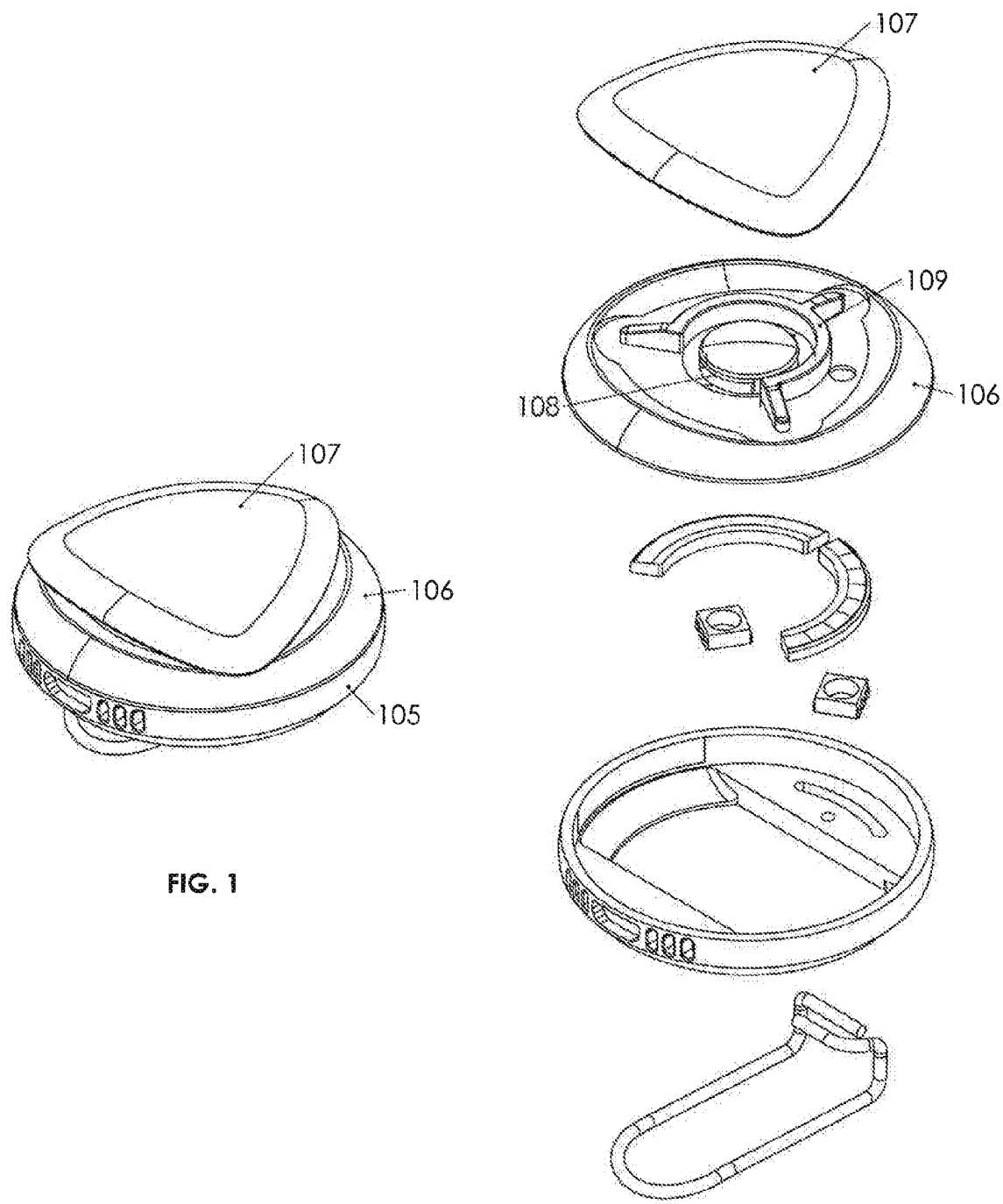
FIG. 1 is a perspective drawing of a particle sensor constructed according to the principles of the present invention.
FIG. 2 is an exploded view of the apparatus of FIG. 1.

One embodiment of the enclosure 905 is illustrated in FIG. 1. The enclosure consists of three or more components which may be ultrasonically welded, screwed, clipped, or otherwise held together (See FIG. 9). These components may be constructed using plastic, but other materials are also suitable. The sensor in FIG. 3 may be partially or fully contained by this enclosure 905 (See also FIGS. 7a-7f and FIG. 9).

The three major components of the enclosure are the bottom cover 105, top cover 106 and a shield 107. Other embodiments may consider just the bottom 105 and top 106 cover. The top or bottom cover may have one or more mounting/access feature for additional sensors. Other embodiments may have significantly different dimensions and geometry than shown in FIG. 1. Additional components may be used inside the enclosure other than the major components to aid in the function of the device.

Figure 9:
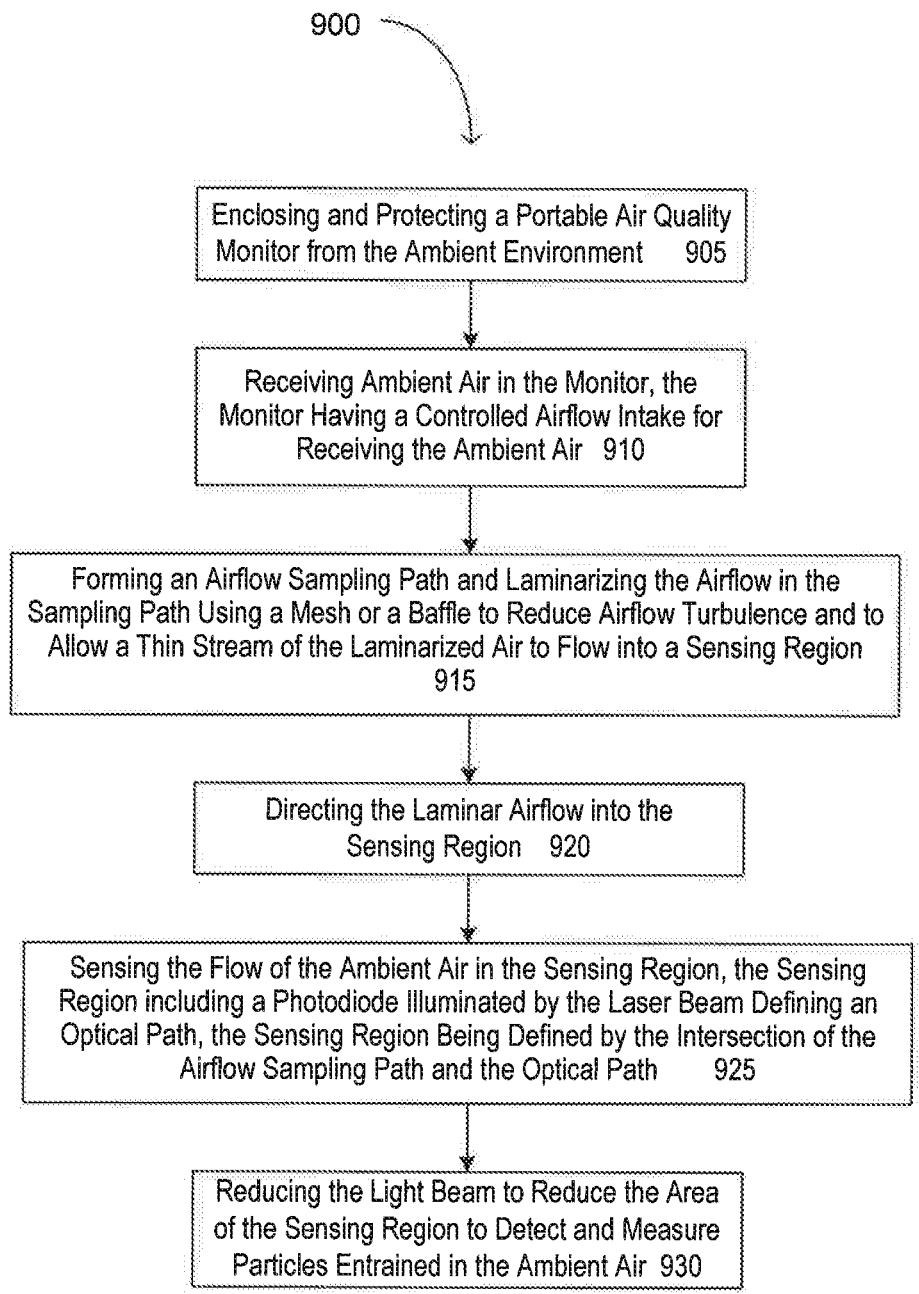
FIG. 9 refers to an execution diagram for the method of detecting and measuring particles in an ambient environment.

Any part of the enclosure 905 may have an engineered surface finish and/or selective metal deposition/plating for aesthetic and/or optical reasons (See FIG. 9). A metal finish may be used to create mirrors 200 for the optical system (See FIGS. 7c-7f). The enclosure may be curved to create mirrors 200 with different optical behaviors. Any part of the enclosure may contain features for directing the airflow for the sensor 905 and 910. Gaskets, flexible plastic, epoxy, tape or other materials may be used to improve the function of these features. Features may be added to any part of the enclosure to reduce or increase intake or outlet airflow velocities 910 (See FIG. 9). Any part of the enclosure may contain overlapping baffles 109 to prevent stray light from reaching the sensor. Any part of the enclosure may be coated or covered with a light-absorbing paint, finish, tape, and/or other material (See FIGS. 7a-7f).

Sensing Region

Figure 3:
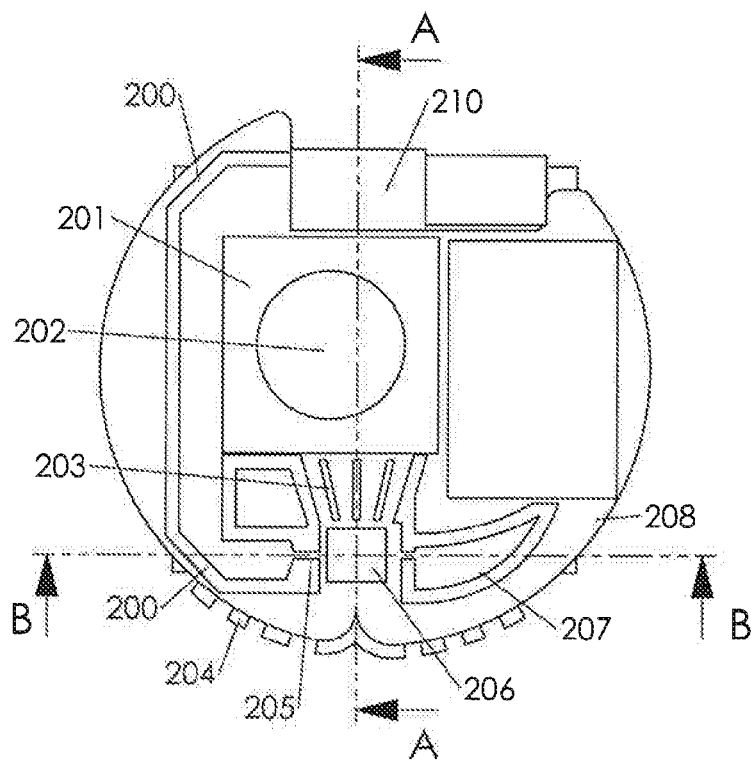
FIG. 3 is a diagrammatic top view of one embodiment of the arrangement of sensor components on the printed circuit board. The intersection between section views A-A and B-B represent the sensing region above the photodiode.
Figure 4:
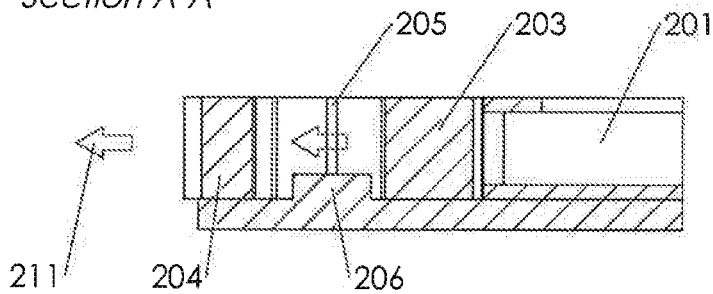
FIG. 4 is a side section view of FIG. 3 of the aerosol sampling path above the photodiode.
Figure 5:
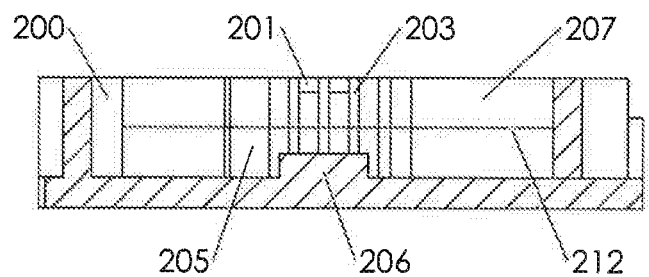
FIG. 5 is a front section view of FIG. 3 of the optical path of the laser above the photodiode.
Figure 6:
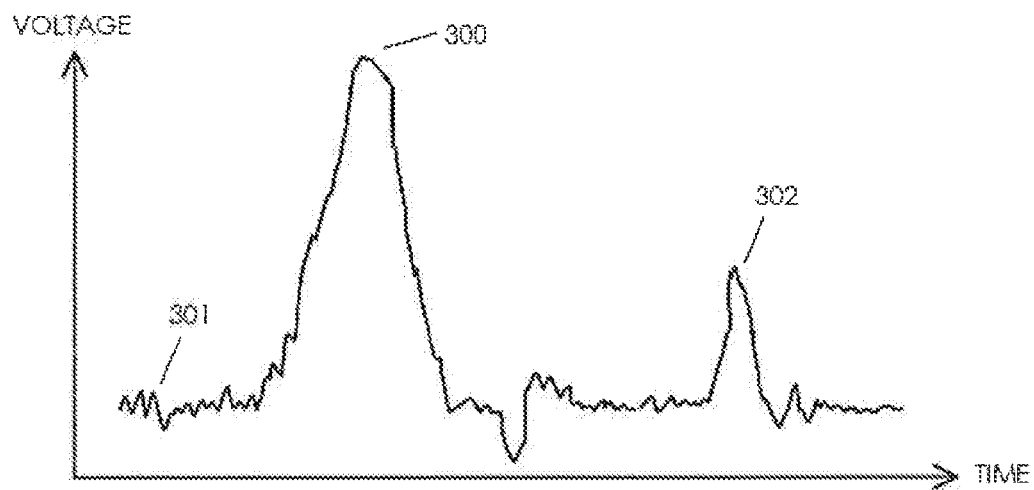
FIG. 6 is an example of a signal pulse output from the photodiode.
Figure 7A:
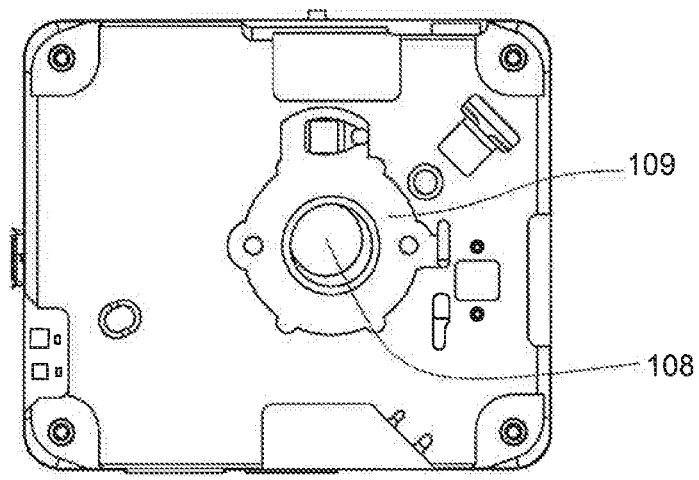
FIGS. 7a-7c provides perspective views of the OPC frame.
Figure 7B:
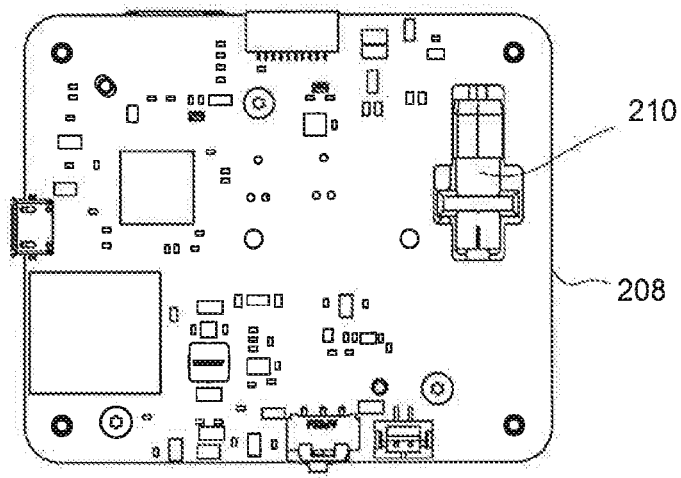
Figure 7C:
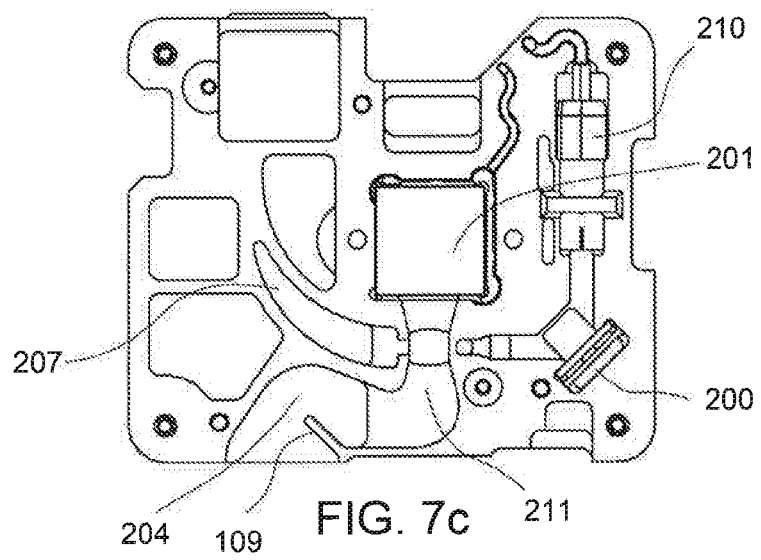
Figure 7D:
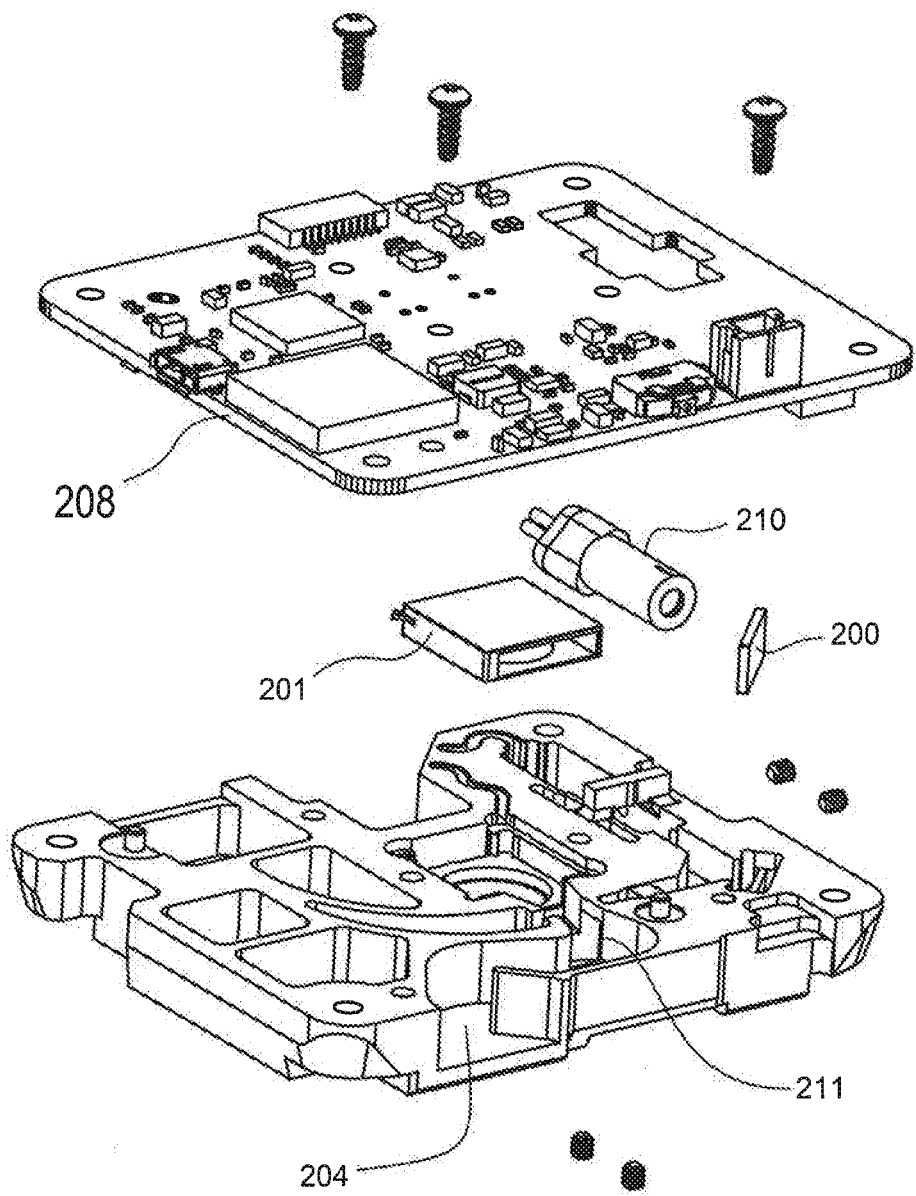
FIG. 7d provides another perspective view of the OPC frame.
Figure 7E:
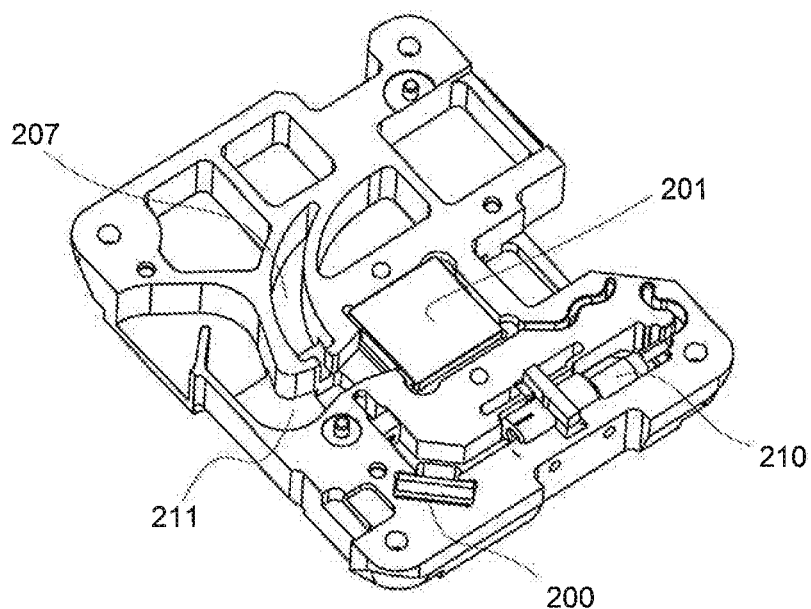
FIGS. 7e-7f provides further perspective views of the OPC frame.
Figure 7F:
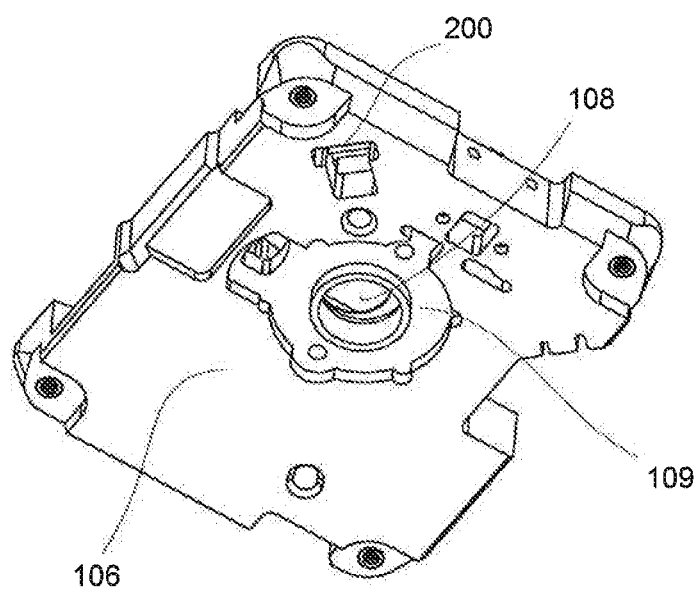

With reference to FIGS. 3, 4 and 5, (See also FIGS. 7a-7f) the sensing region is defined as the intersection between aerosol sampling path 211 and the optical path 212 above the photodiode 206 (See also FIG. 9). In this embodiment, the sensing region is placed at the exhaust of the fan 201. This is done by placing the photodiode 206 at a location downstream from the fan 201, or equivalently at a lower relative pressure than the fan in the aerosol sensing path. However, fan exhausts tend to create turbulent flow which is not ideal for airborne particulate sensing. To mitigate this problem, turbulent airflow from the fan exhaust is laminarized by means of features located at the fan outlet 915 (See FIG. 9). One embodiment uses constriction geometry with mesh or baffles 203 for laminarization 915. In use, these features permit only a thin stream of air over the photodiode and may be placed at an angle perpendicular to the exhaust airflow. The mesh or baffles 203 reduce airflow velocity and thus Reynolds number, thereby reducing the turbulence. The mesh or baffles 203 may also be used to direct the airflow over the photodiode. A plurality of mesh or baffles 203 may be used to increase the effectiveness of laminarization. Double counting due to backflow over the photodiode is minimized by additional features to direct turbulent airflow away from the sensor. One embodiment uses a lower fan pressure and or exhaust velocity to reduce turbulent airflow.

In another embodiment of the invention, the sensing region is located at the inlet of the fan by placing the photodiode upstream from the fan, or equivalently at a higher relative pressure than the fan in the aerosol sensing path. Constriction geometry at the inlet 203 may be used to guide the entirety of the airflow over the photodiode. Features downstream from the constriction 204 may be added to reduce turbulent air flow, thereby reducing coincidence error and double counting errors due to backflow (See FIGS. 7*c*-7*d*).

In this embodiment of the invention, a centrifugal or axial fan 201 is mounted inside the plastic enclosure (See FIGS. 7*c*-7*f*). The fan 201 is used to drive the airborne particulates through the aerosol sampling path 920 (See FIG. 9). The fan 201 may be modified to reduce stray light from entering the sensor. This modification may include coating the fan blades with a light-absorbing paint, finish, tape or other material. The fan casing may be integrated into the enclosure, requiring only a spinning rotor to be installed into the sensor.

In use, the fan 201 may be controlled by means of a closed-loop circuit configuration. The fan 201 may be run at less than 100% duty cycle to allow the control algorithm to properly power the laser beam 210. (See FIGS. 7*b*-7*e*). The control algorithm may be based on a proportional-integral-derivative (PID) control.

In use, the fan 201 may exhaust or intake particles through the sensing region (See FIGS. 7*c*-7*e*). Some embodiments may contain a plurality of fans.

Air Path

The aerosol sampling path 211 is constructed from the interface between the enclosure, fan, any electronics or PCBs and any other physical features inside the enclosure. (See FIGS. 7*a*-7*f*). The aerosol sampling path 211 defines the stream of air that is being measured for entrained particulate (See also FIG. 9). The aerosol sampling path enters through the air intake 108 on the top cover 106 to the fan intake 202. (See FIGS. 7*a* and 7*f*). The low pressure drop through the system is due to the short path length of the aerosol sampling channel and allows the use of smaller fans.

Features for user accessibility may be created in the enclosure to allow user access to selective sections of the aerosol sampling path for cleaning and maintenance. The sensor may be capable of self-cleaning. This may be accomplished with a fan 201 capable of rotating in both directions and operating above its rated voltage and current specifications by means of a control circuit. (See FIGS. 7*c*-7*f*). The fan 201 may be used to clean the device and/or sensor(s). The self-cleaning may be invoked by an algorithm to determine the appropriate cleaning schedule. The cleaning schedule may be a function of previous environmental conditions, sampling frequency of air flow, and/or accuracy of current measurements. Sensing conditions may be integrated into the device's non-volatile memory to determine when the sensor is adversely affected by previous environmental conditions and when cleaning should be conducted by user or device.

Baffles 203, 204 may be incorporated to structure the air flow and control the accumulation of dust and sedimentation. (See FIG. 7*c*-7*d*). One embodiment may have a large device exhaust cross section and/or short air flow path to further reduce sedimentation from fan exhaust to ambient air outside of device.

Laser

A laser 210 is used as a light source to be scattered by entrained particles in the aerosol sampling path as they move through the device. (See FIGS. 7*b*-7*e*). Other optical components may be used to shape and direct the laser beam 210 over the photodiode 206.

The laser 210 may be a laser diode with a built-in or separate driving circuit. (See FIGS. 7*b*-7*e*). It may be in a metallic enclosure for electrostatic and thermal protection. The laser 210 may also have a lens to control the focal length of the laser. One or a plurality of mirrors may be used to fold the beam path, thereby maintaining a specific beam geometry while reducing the physical footprint required by the optics configuration (See also FIG. 9). Components from the enclosure may be used as a baffle, to create an aperture for, or otherwise obstruct stray light from the laser.

The laser 210 may be controlled by means of a circuit board in a closed-loop configuration. The laser 210 may be run at less than 100% duty cycle to allow the control algorithm to properly power the laser 210. The control algorithm may be based on PID control. The laser 210 may be controlled at the same rate as the photodiode 206 is sampled to allow phase locking in high noise or low signal environments (See FIGS. 7*b*-7*e*).

Optical Path

The optical path is defined as the path the laser beam 210 takes through the device and includes all components that interact with this beam. The major components of the optical path may include the following: mirrors, lenses, baffles, apertures and beam dumps or other dissipative features. (See FIGS. 7*b*-7*e*). In this embodiment, the optical path is created with the following components: a single lens with a focal length which may be between 1-10 mm, two mirrors 200 (at 45° angles) used to fold the laser beam 210 to achieve the required beam geometry within a smaller footprint, baffle(s) 109 and aperture(s) 205 as required to prevent stray light from the laser from reflecting directly onto the photodiode 206, and features known as the "beam dump" 207 to dissipate the laser beam after it passes the photodiode. (See FIGS. 7*b*-7*e*). This embodiment of the invention uses a horn geometry 207 to dissipate the laser beam energy and reduce reflections. This feature also prevents stray light from reflecting directly into the photodiode 206. A focusing lens in the optical path may be equipped with a position adjustable lens to dynamically change the laser focal length to improve sensitivity of the sensor for larger and/or smaller particles entrained in the aerosol sampling path. The method for achieving the position adjustment may involve a voice coil, electromagnet, electric motor (DC, AC or stepper), flexure, piezo actuator or other electromechanical motion device. Alternatively, this embodiment of the invention may use one or more mirrors depending on the focal length of the laser. Further, additional mirrors may be advantageously added in order to reduce the required footprint of the overall device.

In other embodiments, a plurality of these components may be used to create the optical path. Other embodiments are described in this section. In addition to their description, the other embodiments may include a plurality of other optical features mentioned in this section.

This and other embodiments may use a beam dump with the following features: a chamber with a simple 45° enclosed corner to dissipate the laser beam energy and reduce reflections, surfaces with a reflective material or coating to reduce dispersion of the reflected beam, and/or surfaces painted or colored to reduce reflected energy.

In one embodiment of the invention, an optical collection system may be used to increase the amount of scattered light sensed by the photodiode 206. In another embodiment of the invention, a parabolic reflector above the primary photodiode 206 may be installed to reflect the scattered light above the photodiode 206 back on to it. In a further embodiment of the invention, a second photodiode may be installed above the primary photodiode 206 by using a flexible PCB to increase the detection of scattered light.

One such embodiment of the invention does not fold the optical path but instead uses a collimating lens and focusing lens with a short focal length which may be between 0.5-3 mm to compress the optical path.

One such embodiment of the invention uses a plurality of mirrors to pass the laser beam back through the air stream over a second photodiode for an additional sensing region. These mirrors may be used to reshape the laser beam geometry for improved detection of larger and/or smaller particles entrained in the aerosol sampling path. Baffles and/or air flow shaping geometry may be implemented to prevent signal cross contamination due to light scattering between the primary and secondary sensing regions.

Flow Sensing

Measuring air flow rate in the aerosol sensing path is necessary to increase the accuracy of particle counting and subsequent conversion to mass concentration 925 (See FIG. 9). The microcontroller unit (MCU), digital signal processor (DSP), or control electronics in the device use air flow rate measurements, which may be used to determine the correlation factor between particle counts and mass concentration, and/or for closed loop control of the fan to increase sensor accuracy and/or reduce the contamination rate of the sensor.

Air flow rate may be sensed through a plurality of the following methods or other methods (See FIG. 9). In one embodiment of the invention, a device using a heating coil and thermistor is placed such that it has sufficient thermal contact with the fluid in the aerosol sampling path. The thermistor may be used to make a measurement of the steady state ambient temperature when the heating coil is driven briefly at a constant power. The rise and decay time of the temperature correlates with the aerosol flow rate near the sensor.

This device may also be used to conduct temperature compensation for the sensor as some components in the device have temperature-dependent responses. This device may be found as an existing electronic component and mounted to the PCB 208. (See FIGS. 7*b* and 7*d*). A plurality of these devices may be placed along the aerosol sampling path 211, before and/or after the photodiode 206, to measure flow rate in critical regions (See FIGS. 7*c*-7*e*).

In one embodiment, a pressure sensing device may be used to determine the air flow by following Poiseuille's Law, stating that the volumetric flow may be found given the pressure difference between two points along the air stream and the viscous resistance. A plurality of these components may be placed before and/or after the photodiode 206 and along the aerosol sampling path 211 to measure flow in critical regions (See FIGS. 7*c*-7*e*). This device may be found as an existing electronic component and mounted to the PCB 208 (See FIGS. 7*b*-7*e*).

In one embodiment, airflow is inferred from the rotational speed of the fan 201 (See FIGS. 7*c*-7*e*). Rotational speed of the fan 201 may be measured by means of a pulse count or analog voltage from an optical sensor, Hall-effect sensor, or other odometer connected to or integrated with the fan 201; measurement of the total current, voltage or power consumption of the fan; and/or pulse counting of the peak current and/or voltage drawn by the fan 201.

In one embodiment, the amplifier signal peaks 300 may be analyzed to determine flow rate. A peak in the signal 300 indicates a particle and the width of the given peak indicates air flow rate. A larger width represents slower airflow and/or a larger particle. This analysis may be integrated with the particle detection and sizing algorithms implemented in the control electronics, MCU and/or DSP.

Electrical

In this embodiment of the invention, a circuit board 208 is used to mount the various electrical components of the sensor. (See FIGS. 7*b*-7*d*). A photodiode 206 is mounted, in a fashion known to those skilled in the art, to a PCB at the intersection between the laser beam 210 and the aerosol sampling path 211 (See also FIG. 9). The photodiode 206 creates a small current upon sensing light. Another embodiment may have a second photodiode located on the other side of the laser beam 210 relative to the first photodiode 206 attached to a flexible PCB constrained by enclosure features (See also FIGS. 7*b*-7*e*).

Referring now to FIG. 8 (805), a software flowchart is illustrated for the sample input. For instance, an amplifier circuit, designed in a fashion known to those skilled in the art, may be mounted near the photodiode 206. A high gain current-to-voltage converter (i.e., a transimpedance amplifier) may be used to amplify the voltage output of the photodiode one or more times into a usable voltage. The circuitry may include an analog low-pass filter with one or more poles. The amplifier may have a plurality of stages which may be AC or DC coupled. The amplifier may be used for analog filtering of the photodiode signal.

An analog to digital converter is mounted on the PCB and converts the filtered or unfiltered amplifier voltage to a digital signal. The analog signal in FIG. 6 is comprised of peaks 300 which represent the light reflected by the airborne particular matter and sensed by the photodiode 206.

The analog signal also has background noise 301 in the form of: quantum noise (shot noise), stray light noise, electromagnetic interference, and other forms of noise or interference. Shielding from the noise 301 is provided where possible. Active or passive low-pass analog filtering may be used to reduce signal noise 301. The peak detection and sizing algorithm is calibrated to account for this noise.

The analog signal contains peaks 300, 302 indicating partial or multiple particles crossing the sensing area. These are referred to as boundary and coincidence errors and may be exempted from counting by the peak detection and sizing algorithm. One peak is associated with one particle in the absence of boundary or coincidence errors. The height of the peak correlates with albedo, the reflecting power of a surface, and the particle size.

The sampling frequency of the ADC depends on the shape of the pulses generated by the sensor. The peak shape may be influenced by the following components or effects: the photodiode, the amplifier, laser beam width, air flow rate, air flow cross section, humidity, temperature, particle diameter, particle albedo, and other effects.

Control electronics, MCU, or DSP may be used to process the digital signal. The PCB may contain amplifier and control electronics for the fan and laser that are controlled by the MCU or DSP. The MCU or DSP may contain all features required to function, including non-volatile memory for firmware, calibration settings, and device state information.

In this embodiment of the invention, the control electronics may decide to enter a low power mode based on user input and/or results from the peak detection and sizing algorithm. One embodiment of a low power sensing mode may involve a reduced sampling time to reduce the duty cycle of the device and extend battery life. In poor air conditions, less logging is needed to obtain a statistically accurate measurement. To perform this, the control electronics turn the sensor on and sample the air for a standard sampling duration. If the count threshold is exceeded, the next sampling duration is reduced. To confirm the statistical significance of the sampling duration, a standard duration sample is taken for every 1-20 low power samples. If the particle load is found to have decreased below the threshold, the sampling duration is increased again.

Another low power sensing mode involves using pulse width modulation of the laser and/or fan. In this mode, the laser and/or fan are run at less than 100% duty cycle to reduce their current draw by means of control electronics. Lower sampling rates may be sufficient if the peak amplitude is sufficiently high above the background noise or if the air is sufficiently dirty. Again, a standard sample needs to be taken for every 1-20 low power samples to ensure sensor accuracy is maintained.

In this embodiment one or more flexible circuit boards may be used to locate electronics inside the enclosure. Other embodiments may have one or more of the following: PCBs, photodiodes, amplifier circuits, ADCs, MCUs, and/or DSPs 810 (See FIG. 8).

Algorithms

The control electronics, MCU and/or DSP employ a peak detection and sizing algorithm to size and count particles from the amplifier signal. For this embodiment, the algorithm may include, but is not limited to, signal smoothing, baseline correction, peak detection, and peak sizing. The raw output signal from the photodiode is subjected to noise; signal smoothing is required to transform the pulse into a usable signal. This embodiment may involve, but is not limited to, the following algorithms.

In one embodiment of the invention, wavelet-based filters such as discrete or continuous wavelet transforms may be used for signal smoothing and peak detection. Wavelet-based filters are advantageous for peak detection because the wavelet may be dynamically crafted to correlate a range of peak widths. In particular, continuous wavelet transforms provide optimal performance among other algorithms due to the use of wavelets in baseline modeling/correcting, in addition to the use of ridge lines.

In one embodiment, the Savitzky-Golay filter may be used for the signal smoothing procedure 815. It may be thought of as a generalized moving average filter, performing a least squares fit of a subset of adjacent data points to a polynomial. The output is the central point of the fitted polynomial curve 815. (See FIG. 8).

In one embodiment, a regular moving average filter (weighted or un-weighted) may be used. It is an alternative smoothing algorithm with a simplified implementation, such that increasing the filter width increases the smoothing effect of the signal.

Figure 8:
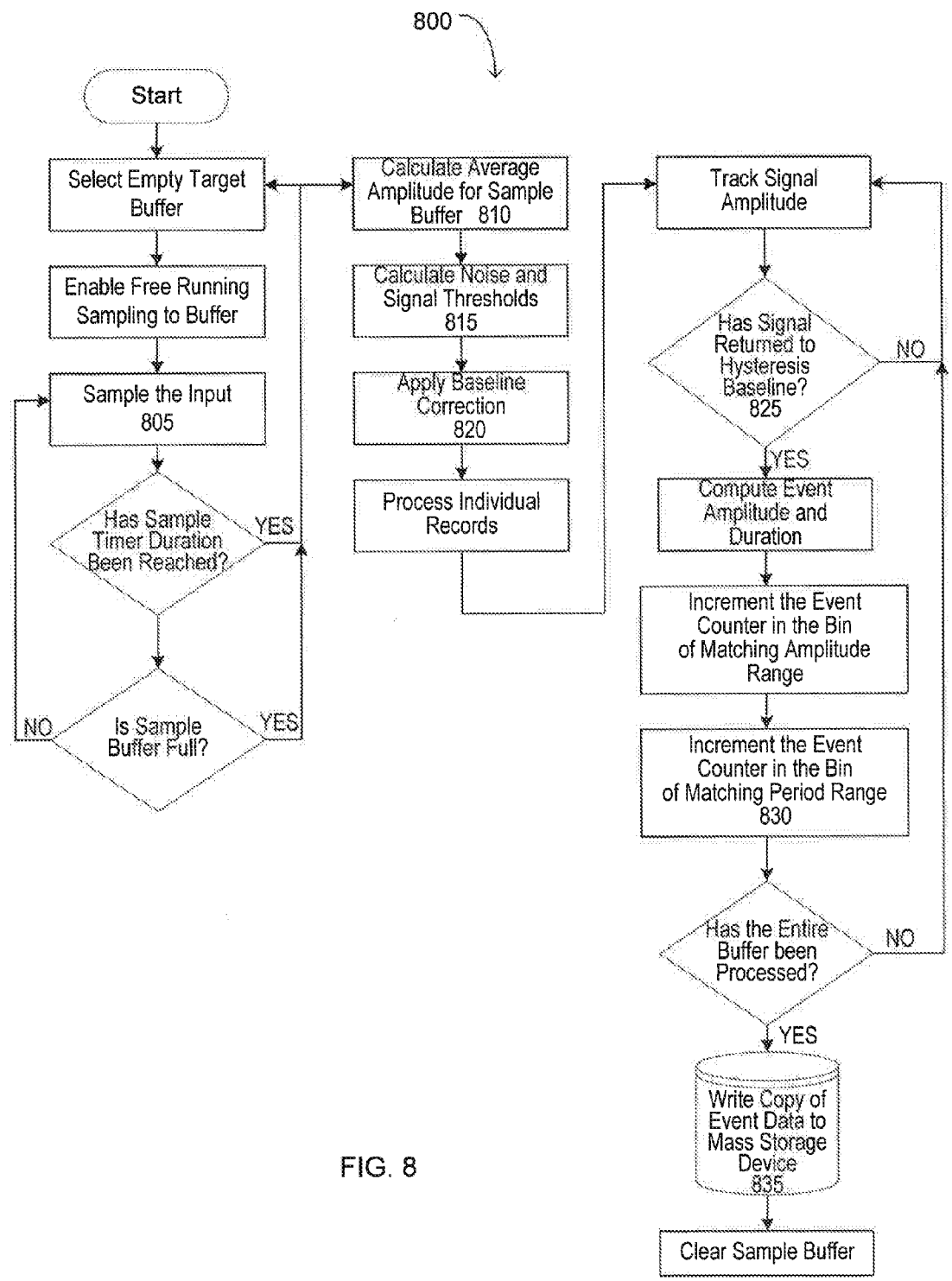
FIG. 8 illustrates a software flowchart for the Algorithms section.

In one embodiment of the invention, an approximated bi-rectangular filter, computed as a recursive filter, may be implemented 820 (See FIG. 8).

Digital baseline correction algorithms may also be necessary as part of the peak detection and sizing algorithm. Dark current and optical/stray light background noise may be actively adjusted to and subtracted from the data set by taking periodically taking dark sensor readings. A dark sensor reading is when the laser and fan are turned off and the signal on the photodiode is measured. These measurements are averaged and may be subtracted from a reading taken when the sensor is active (i.e. the laser and fan are on). This baseline adjustment may be done every time the device is turned on or between measurements when the duty cycle is less than 100%.

The continuous wavelet transform may also be used to model the baseline. If a symmetric wavelet function is used, the continuous wavelet transform automatically removes the baseline.

In one embodiment, the algorithm may track historical baseline adjustments to determine if cleaning is required or if the device is damaged 825, 830 (See FIG. 8).

After signal smoothing, digital peak detection may be carried out with a plurality of the following algorithms, or other algorithms not specified. A peak may be detected each time the signal exceeds the amplitude threshold for a given duration. The threshold may change dynamically depend on the current noise level. The peak duration may have high and low thresholds to prevent false positives. Once a peak is considered valid, the particle may be counted in a specific bin size based on the peak height and width. Peak detection may also be conducted by time reversed convolution with reference peaks. One reference peak (or kernels) is required for each sizing bin. When a reference peak has a sufficient correlation factor with a kernel, a particle is detected and may be counted in the size bin associated with that kernel. This method has the advantage of being able to handle boundary and coincidence errors succinctly when the correct correlation factor thresholds are chosen.

In another embodiment of the invention, peak detection is conducted by means of a fast Fourier transform. In the Fourier domain, valid particles sit within the expected frequency thresholds and have sufficient amplitude to be recognized above the background noise. When these requirements are met, a particle may be counted in the bin size associated with the corresponding frequency and amplitude thresholds 835 (See FIG. 8). This method has the additional benefit of clearly separating high frequency background noise from the given signal.

Thresholds for any algorithm may be dictated by a reference or look-up table stored in non-volatile memory 835. The MCU, DSP or control electronics store the counts in non-volatile memory until the data is pushed or pulled off the sensor by its host 835. Data may be overwritten in reverse chronological order if the logging duration exceeds memory capacity. Calibration of the algorithm may be accomplished by assuming a monotonic relationship between the scattered light intensity and the particle size.

A calibration procedure may involve sampling aerosols of monodispersed or polydispersed particulate. Monodispersed particulate has a tight and well known size, size distribution, and refractive index. Polydispersed particulate with a known refractive index may also be used if the probabilistic size distribution is well known. The advantages of using polydispersed over monodispersed particulate are the increased availability and reduced cost. The sensor sampling may be adjusted by a scaling factor that provides the optimal match between the measured size distribution and the expected distribution of the monodispersed or polydispersed particulate.

Further calibration may be accomplished in the form of temperature and humidity scaling factors. Further calibration and scaling factors may be added to change the data from particle counts to mass concentration. A plurality of the following measurements may be used to determine mass concentration, including but not limited to: flow rate, temperature, and humidity.

It should be understood that the foregoing relates to various embodiments of the invention and that modifications may be made without departing from the spirit and scope of the invention. It should also be understood that the present invention is not limited to the designs mentioned in this application and the equivalent designs in this description, but it is also intended to cover other equivalents now known to those skilled in the art, or those equivalents which may become known to those skilled in the art in the future.

INDUSTRIAL APPLICABILITY

The invention pertains to a portable device for detecting and measuring particles entrained in ambient air, which may be of value or importance to various industries such as emissions controls and/or air quality control for research and/or personal health.

What is claimed is:

1. A portable ambient air quality monitor comprising:
   an enclosure to enclose and protect the monitor from an ambient environment, the enclosure having a top, a side and a bottom and configured to define an airflow sampling path, an optical path and a sensing region,
   the airflow sampling path having an airflow intake and an air channel connected to the airflow intake and an airflow outlet connected to the air channel,
     the airflow sampling path configured to allow a sampling airflow to enter the monitor through the airflow intake, pass through the air channel and exit the monitor through the airflow outlet,
   the air channel having
     a curved configuration to prevent light entering the airflow sampling path through the airflow intake from passing therethrough and
     having at least one baffle within the airflow sampling path proximate the airflow intake to prevent light entering the airflow sampling path through the airflow intake from passing therethrough and for laminarizing the sampling airflow in the air sampling path,
   the airflow intake being configured to be perpendicular to the airflow outlet;
   the optical path being defined by a photodiode illuminated by a laser beam;
   the sensing region being defined by the intersection of the airflow sampling path and the optical path; and
   a sensor within the sensing region to detect and measure particles entrained in the sample airflow.

2. The portable ambient air quality monitor according to claim 1, wherein the enclosure further includes a shield to attenuate internal and external light before reaching the sensing region.

3. The portable ambient air quality monitor according to claim 1, wherein the airflow pressure in the sensing region is higher than the airflow pressure at the airflow intake.

4. The portable ambient air quality monitor according to claim 1, wherein the baffle is configured to laminarize the airflow over the photodiode.

5. The portable ambient air quality monitor according to claim 1, wherein the sensor further includes a fan disposed near the airflow intake, the fan being configured to direct the airflow into the sensing region in one direction for sensing particles in the ambient air, and in a second direction for removing particles from the sensing region.

6. The portable ambient air quality monitor according to claim 5, wherein the fan includes blades coated with a light absorbing coating to reduce stray light from entering the sensing region.

7. The portable ambient air quality monitor according to claim 6, wherein the light-absorbing coating is paint or tape.

8. The portable ambient air quality monitor according to claim 1, wherein the sensing region includes at least one lens having an adjustable focal length, wherein the focal length can be varied between 1-10 mm away from its nominal focal length for sensing larger or smaller particles.

9. The portable ambient air quality monitor according to claim 1, wherein the optical path includes at least one mirror disposed at 45 degree angles to fold the laser beam to form a beam having a smaller footprint at the surface of the photodiode.

10. The portable ambient air quality monitor according to claim 1, wherein the optical path includes at least one baffle and at least one aperture to prevent stray light from the source of the beam from being directed onto the photodiode.

11. The portable ambient air quality monitor according to claim 1, wherein the optical path includes at least one beam dump to dissipate the laser energy and reduce reflection after the laser beam passes through the photodiode.

12. The portable ambient air quality monitor according to claim 11, wherein the beam dump includes a horn geometry configuration to prevent stray light from being directed onto the photodiode.

13. The portable ambient air quality monitor according to claim 11, wherein the beam dump further includes a chamber with a 45 degree enclosed corner to further dissipate the laser beam energy and to reduce reflection.

14. A method for detecting and measuring particles m an ambient environment, the method comprising the steps of:
   enclosing and protecting a portable air quality monitor from the ambient environment;
   configuring the monitor to have an airflow sampling path and an optical path,
     the airflow sampling path having an airflow intake and an air channel connected to the airflow intake and an airflow outlet connected to the air channel,
     the optical path being defined by a photodiode illuminated by a laser beam;
   configuring the airflow sampling path and an optical path to intersect to define a sensing region;
   configuring the airflow sampling path to allow a sampling airflow to enter the monitor through the airflow intake, pass through the air channel and exit the monitor through the airflow outlet;
   configuring the air channel to have a curved configuration and to have at least one baffle within the airflow sampling path proximate the airflow intake to prevent light entering the airflow sampling path through the airflow intake from passing therethrough;

configuring the at least one baffle to laminarize the sampling airflow in the air sampling path to allow a thin stream of the laminarized air to flow into the sensing region;

directing the laminar airflow into the sensing region;

sensing the laminar airflow in a sensing region; and reducing the light beam to reduce the area of the sensing region to detect and measure particulate matter floating in the ambient air.

\* \* \* \* \*